United States Patent
Mua et al.

(10) Patent No.: US 9,661,876 B2
(45) Date of Patent: May 30, 2017

(54) SUGAR-ENRICHED EXTRACT DERIVED FROM TOBACCO

(71) Applicant: R.J. REYNOLDS TOBACCO COMPANY, Winston-Salem, NC (US)

(72) Inventors: John-Paul Mua, Advance, NC (US); Barry Bratcher, Owensboro, KY (US); Kyle Ford, Germanton, NC (US); Leigh Hagan, Owensboro, KY (US); Leigh Ann Blevins Joyce, Lewisville, NC (US); Joshua D. Morton, Evansville, IN (US); Samuel Mark Debusk, Lexington, NC (US); Margarette Elisa Lovette, Winston-Salem, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 354 days.

(21) Appl. No.: 13/829,086

(22) Filed: Mar. 14, 2013

(65) Prior Publication Data

US 2014/0271951 A1    Sep. 18, 2014

(51) Int. Cl.
*A61K 36/81* (2006.01)
*A24B 15/24* (2006.01)
*A23L 1/30* (2006.01)
*A23L 2/52* (2006.01)
*A61K 8/97* (2017.01)
*A23K 20/163* (2016.01)

(52) U.S. Cl.
CPC .......... *A24B 15/241* (2013.01); *A23K 20/163* (2016.05); *A23L 1/3002* (2013.01); *A23L 2/52* (2013.01); *A61K 8/97* (2013.01); *A61K 36/81* (2013.01)

(58) Field of Classification Search
None
See application file for complete search history.

(56) References Cited

U.S. PATENT DOCUMENTS

| | | |
|---|---|---|
| 4,244,381 A | 1/1981 | Lendvay |
| 2007/0137663 A1 | 6/2007 | Taylor et al. |
| 2007/0193596 A1 | 8/2007 | Mori et al. |
| 2008/0254149 A1 | 10/2008 | Havkin-Frenkel |
| 2011/0092684 A1* | 4/2011 | Abelyan et al. ............. 536/18.1 |
| 2011/0174323 A1 | 7/2011 | Coleman, III et al. |
| 2011/0259353 A1 | 10/2011 | Coleman, III et al. |
| 2012/0141648 A1 | 6/2012 | Morton et al. |
| 2012/0152265 A1 | 6/2012 | Dube et al. |
| 2012/0192880 A1 | 8/2012 | Dube et al. |
| 2012/0192882 A1 | 8/2012 | Dube et al. |
| 2012/0211016 A1 | 8/2012 | Byrd, Jr. et al. |
| 2012/0272976 A1 | 11/2012 | Byrd, Jr. et al. |
| 2013/0276801 A1 | 10/2013 | Byrd, Jr. et al. |
| 2014/0096780 A1 | 4/2014 | Gerardi |

FOREIGN PATENT DOCUMENTS

JP     1162008    10/1997

* cited by examiner

*Primary Examiner* — Terry A McKelvey
*Assistant Examiner* — Catheryne Chen
(74) *Attorney, Agent, or Firm* — Womble Carlyle Sandridge & Rice, LLP

(57) ABSTRACT

The present disclosure describes methods of obtaining and/or deriving a sugar-enriched extract from plants of the *Nicotiana* species and methods for incorporation of such extracts into various tobacco compositions. One exemplary method for preparing a sugar-enriched extract comprises contacting *Nicotiana* plant material with a solvent and extracting sugars into the solvent to form a liquid sugar-containing extract; separating a solid extracted plant material from the liquid sugar-containing extract; clarifying the liquid sugar-containing extract to form a clarified sugar-containing extract and a solids fraction; and isolating the liquid sugar-containing extract to provide a sugar-enriched extract comprising a combined weight of fructose and glucose of at least about 10% by dry weight. In certain embodiments, the sugars of the extract comprise at least about 50% by weight fructose.

24 Claims, 4 Drawing Sheets

SUGAR-ENRICHED EXTRACT DERIVED FROM TOBACCO

FIELD OF THE INVENTION

The present invention relates to products made or derived from tobacco, or that otherwise incorporate tobacco or components of tobacco, and are intended for human consumption. Of particular interest are ingredients or components obtained or derived from plants or portions of plants from the *Nicotiana* species.

BACKGROUND OF THE INVENTION

Cigarettes, cigars, and pipes are popular smoking articles that employ tobacco in various forms. Such smoking articles are employed by heating or burning tobacco to generate aerosol (e.g., smoke) that may be inhaled by the smoker. Popular smoking articles, such as cigarettes, have a substantially cylindrical rod shaped structure and include a charge, roll or column of smokable material such as shredded tobacco (e.g., in cut filler form) surrounded by a paper wrapper thereby forming a so-called "tobacco rod." Normally, a cigarette has a cylindrical filter element aligned in an end-to-end relationship with the tobacco rod. Typically, a filter element comprises plasticized cellulose acetate tow circumscribed by a paper material known as "plug wrap." Certain cigarettes incorporate a filter element having multiple segments, and one of those segments can comprise activated charcoal particles. Typically, the filter element is attached to one end of the tobacco rod using a circumscribing wrapping material known as "tipping paper." It also has become desirable to perforate the tipping material and plug wrap, in order to provide dilution of drawn mainstream smoke with ambient air. A cigarette is employed by a smoker by lighting one end thereof and burning the tobacco rod. The smoker then receives mainstream smoke into his/her mouth by drawing on the opposite end (e.g., the filter end) of the cigarette.

The tobacco used for cigarette manufacture is typically used in blended form. For example, certain popular tobacco blends, commonly referred to as "American blends," comprise mixtures of flue-cured tobacco, burley tobacco and Oriental tobacco, and in many cases, certain processed tobaccos, such as reconstituted tobacco and processed tobacco stems. The precise amount of each type of tobacco within a tobacco blend used for the manufacture of a particular cigarette brand varies from brand to brand. However, for many tobacco blends, flue-cured tobacco makes up a relatively large proportion of the blend, while Oriental tobacco makes up a relatively small proportion of the blend. See, for example, *Tobacco Encyclopedia*, Voges (Ed.) p. 44-45 (1984), Browne, *The Design of Cigarettes*, 3$^{rd}$ Ed., p. 43 (1990) and *Tobacco Production, Chemistry and Technology*, Davis et al. (Eds.) p. 346 (1999).

Tobacco also may be enjoyed in a so-called "smokeless" form. Particularly popular smokeless tobacco products are employed by inserting some form of processed tobacco or tobacco-containing formulation into the mouth of the user. See for example, the types of smokeless tobacco formulations, ingredients, and processing methodologies set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2005/0244521 to Strickland et al.; 2006/0191548 to Strickland et al.; 2007/0062549 to Holton, Jr. et al.; 2007/0186941 to Holton, Jr. et al.; 2007/0186942 to Stricldand et al.; 2008/0029110 to Dube et al.; 2008/0029116 to Robinson et al.; 2008/0029117 to Mua et al.; 2008/0173317 to Robinson et al.; 2008/0196730 to Engstrom et al.; 2008/0209586 to Neilsen et al.; 2008/0305216 to Crawford et al.; 2009/0025738 to Mua et al.; 2009/0025739 to Brinkley et al.; 2009/0065013 to Essen et al.; 2009/0293889 to Kumar et al.; 2010/0018540 to Doolittle et al; 2010/0018541 to Gerardi et al.; 2010/0291245 to Gao et al; 2011/0139164 to Mua et al.; 2011/0174323 to Coleman, III et al.; 2011/0247640 to Beeson et al.; 2011/0259353 to Coleman, III et al.; 2012/0037175 to Cantrell et al.; 2012/0055494 to Hunt et al.; 2012/0103353 to Sebastian et al.; 2012/0125354 to Byrd et al.; 2012/0138073 to Cantrell et al.; and 2012/0138074 to Cantrell et al; PCT WO 04/095959 to Arnarp et al.; PCT WO 05/063060 to Atchley et al.; PCT WO 05/004480 to Engstrom; PCT WO 05/016036 to Bjorkholm; PCT WO 05/041699 to Quinter et al., and PCT WO 10/132444 to Atchley; each of which is incorporated herein by reference.

One type of smokeless tobacco product is referred to as "snuff." Representative types of moist snuff products, commonly referred to as "snus," have been manufactured in Europe, particularly in Sweden, by or through companies such as Swedish Match AB, Fiedler & Lundgren AB, Gustavus AB, Skandinavisk Tobakskompagni A/S, and Rocker Production AB. Snus products available in the U.S.A. have been marketed under the tradenames Camel Snus Frost, Camel Snus Original and Camel Snus Spice by R. J. Reynolds Tobacco Company. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard. Representative smokeless tobacco products also have been marketed under the tradenames Oliver Twist by House of Oliver Twist A/S; Copenhagen moist tobacco, Copenhagen pouches, Skoal Bandits, Skoal Pouches, SkoalDry, Rooster, Red Seal long cut, Husky, and Revel Mint Tobacco Packs by U.S. Smokeless Tobacco Co.; Marlboro Snus and "taboka" by Philip Morris USA; Levi Garrett, Peachy, Taylor's Pride, Kodiak, Hawken Wintergreen, Grizzly, Dental, Kentucky King, and Mammoth Cave by American Snuff Company, LLC; Camel Snus, Camel Orbs, Camel Sticks, and Camel Strips by R. J. Reynolds Tobacco Company. Other exemplary smokeless tobacco products that have been marketed include those referred to as Kayak moist snuff and Chatanooga Chew chewing tobacco by Swisher International, Inc.; and Redman chewing tobacco by Pinkerton Tobacco Co. LP.

Through the years, various treatment methods and additives have been proposed for altering the overall character or nature of tobacco materials utilized in tobacco products. For example, additives or treatment processes have been utilized in order to alter the chemistry or sensory properties of the tobacco material, or in the case of smokable tobacco materials, to alter the chemistry or sensory properties of mainstream smoke generated by smoking articles including the tobacco material. The sensory attributes of cigarette smoke can be enhanced by incorporating flavoring materials into various components of a cigarette. Exemplary flavoring additives include menthol and products of Maillard reactions, such as pyrazines, aminosugars, and Amadori compounds. American cigarette tobacco blends typically contain a casing composition that includes flavoring ingredients, such as licorice or cocoa powder and a sugar source such as high fructose corn syrup. See also, Leffingwell et al., *Tobacco Flavoring for Smoking Products*, R.J. Reynolds Tobacco Company (1972), which is incorporated herein by reference. In some cases, treatment processes involving the use of heat can impart to the processed tobacco a desired color or visual character, desired sensory properties, or a desired physical nature or texture. Various processes for preparing flavorful and aromatic compositions for use in tobacco compositions are set forth in U.S. Pat. No. 3,424,171 to Rooker; U.S. Pat. No. 3,476,118 to Luttich; U.S. Pat. No. 4,150,677 to Osborne, Jr. et al.; U.S. Pat. No. 4,986,286 to Roberts et al.; U.S. Pat. No. 5,074,319 to White et al.; U.S. Pat. No. 5,099,862 to White et al.; U.S. Pat. No. 5,235,992 to Sensabaugh, Jr.; U.S. Pat. No. 5,301,694 to Raymond et al.; U.S. Pat. No. 6,298,858 to Coleman, III et al.; U.S. Pat. No. 6,325,860 to Coleman, III et al.; U.S. Pat. No. 6,428,624 to Coleman, III et al.; U.S. Pat. No. 6,440,223 to Dube et al.; U.S. Pat. No. 6,499,489 to Coleman, III; and U.S. Pat. No. 6,591,841 to White et al.; US Pat. Appl. Pub. Nos. 2004/0173228 to Coleman, III and 2010/0037903 to Coleman, III et al., each of which is incorporated herein by reference.

The sensory attributes of smokeless tobacco can also be enhanced by incorporation of certain flavoring materials. See, for example, US Pat. Appl. Pub. Nos. 2002/0162562 to Williams; 2002/0162563 to Williams; 2003/0070687 to Atchley et al.; 2004/0020503 to Williams, 2005/0178398 to Breslin et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Neilsen et al., each of which is incorporated herein by reference.

It would be desirable to provide additional compositions and methods for altering the character and nature of tobacco (and tobacco compositions and formulations) useful in the manufacture of smoking articles and/or smokeless tobacco products.

SUMMARY OF THE INVENTION

The present invention provides materials from *Nicotiana* species (e.g., tobacco-derived materials) comprising components from plants of the *Nicotiana* species useful for incorporation into tobacco compositions utilized in a variety of tobacco products, such as smoking articles and smokeless tobacco products. The invention also provides methods for extracting components from *Nicotiana* species (e.g., tobacco materials), and methods for processing those components and tobacco materials incorporating those components.

In particular, the invention provides sugar-enriched materials derived from tobacco materials, methods of obtaining and/or deriving such sugar-enriched materials, and methods for incorporation of such sugar-enriched materials into various tobacco compositions. In certain embodiments, the invention provides a sugar-enriched extract and in certain embodiments, the invention provides high fructose tobacco-derived sugar-enriched extracts, including tobacco-derived sugar-enriched extracts wherein the sugar component comprises at least about 50% fructose by weight.

In one aspect of the disclosure is provided a method for preparing a sugar-enriched extract from a plant of the *Nicotiana* species or portion thereof, comprising: receiving a plant material of the *Nicotiana* species; contacting the plant material with a solvent for a time and under conditions sufficient to extract one or more sugars from the plant material into the solvent and form a liquid sugar-containing extract; separating a solid extracted plant material from the liquid sugar-containing extract; clarifying the liquid sugar-containing extract to form a clarified sugar-containing extract and a solids fraction; and isolating the clarified sugar-containing extract to give a sugar-enriched extract comprising at least about 10% fructose and glucose by dry weight. The solvent can vary and may, for example, comprise water.

In another aspect of the disclosure is provided a method for preparing a sugar-enriched extract from a plant of the *Nicotiana* species or portion thereof, comprising: receiving a plant material of the *Nicotiana* species; pressing the plant material in the absence of added liquid and collecting a liquid sugar-containing extract released from the pressed plant material; separating a solid plant material from the liquid sugar-containing extract; clarifying the liquid sugar-containing extract to form a clarified sugar-containing extract and a solids fraction; and isolating the clarified sugar-containing extract to give a sugar-enriched extract comprising at least about 10% fructose and glucose by dry weight.

The plant material of the *Nicotiana* species to which the methods provided herein can be applied can comprise, for example, green plant material, yellowed plant material, cured plant material, or a combination thereof. In some embodiments, a higher percentage of fructose and glucose by dry weight is obtained according to the methods described herein. For example, the sugar-enriched extract may in some embodiments comprise at least about 20% or at least about 30% fructose and glucose by dry weight. In certain embodiments, the at least about 10% fructose and glucose in the sugar-enriched extract comprises at least about 50% fructose by weight in the absence of any further treatment to convert any portion of glucose to fructose.

In some embodiments, the clarifying step comprises filtering the liquid sugar-containing extract. The filtering can comprise, for example, one or more of microfiltration, ultrafiltration, and nanofiltration.

Various additional methods can be used in combination with the above processes. For example, in certain embodiments, the methods described herein can further comprise adjusting the pH of the clarified sugar-containing extract to a pH of at least about 8. In some embodiments, the methods can further comprise concentrating the clarified sugar-containing extract to provide a concentrated sugar-enriched extract. Concentration can be conducted using, for example, one or more of reverse osmosis, vacuum evaporation, and atmospheric heating. Concentrating can provide a sugar-enriched extract having certain characteristics. The resulting extract can be, for example, in the foam of a liquid, semi-solid, or solid. The extract can have any level of solids content therein, e.g., a total solids content of at least about 50%, e.g., at least about 60% by weight. In some embodiments, the sugar (i.e., fructose and glucose) present in the sugar-enriched extract comprises at least about 50% fructose by weight in the absence of any further treatment to convert any portion of glucose to fructose.

The method can, in some embodiments, further comprise adding one or more components to remove color, odor, taste, alkaloids, metals, or a combination thereof, at any step of the process. The one or more components may, for example, be selected from the group consisting of activated carbon, a resin, clay, a chelating agent, a molecularly imprinted polymer, a non-imprinted polymer, or a combination thereof.

In certain embodiments, the method further comprises treating the solids fraction obtained from the clarifying step to convert at least a portion of the starch contained therein to sugar to give a treated solids fraction; and concentrating the treated solids fraction. The treated solids fraction may optionally be combined with the sugar-enriched extract obtained as described herein. In some embodiments, the treating step comprises one or both of heating (e.g., boiling) the solids fraction at an acidic pH and adding one or more enzymes to the solids fraction. The one or more enzymes can be, for example, selected from the group consisting of α-amylase, amyloglucosidase, and xylose isomerase. The method may further comprise, in certain embodiments, filtering the treated solids fraction prior to said concentrating. The concentrating step may provide a product in various forms, including but not limited to, the form of a liquid, semi-solid, or solid.

In one further aspect, the disclosure provides a sugar-enriched extract obtained according to any of the methods described herein. Certain sugar-enriched extracts described herein can be characterized as comprising less than about 2% by weight nicotine (e.g., less than about 1% by weight nicotine). In a further aspect, the disclosure provides a tobacco composition for use in a smoking article, smokeless tobacco product, or aerosol-generating device, comprising a sugar-enriched extract as described in the present disclosure. The disclosure further encompasses dietary supplements, foods, beverages, personal care items, pharmaceutical products, and/or pet food comprising the sugar-enriched extract obtained according to the methods provided herein.

In one additional aspect, the disclosure provides a sugar-enriched extract derived from a plant of the *Nicotiana* species, wherein the extract comprises at least about 10% fructose and glucose by dry weight. The fructose and glucose content can, in some embodiments, be higher, e.g., at least about 20%, at least about 30%, at least about 40%, at least about 50%, or at least about 60% by dry weight. The extract can be, for example, in the form of a liquid, semi-solid, or solid. The extract can have any level of solids content therein, e.g., a total solids content of at least about 50%, such as at least about 60% by weight. In some embodiments, the sugar (i.e., fructose and glucose) present in the sugar-enriched extract comprises at least about 50% fructose by weight in the absence of any further treatment to convert any portion of glucose to fructose. In certain embodiments, the sugar-enriched extract can be characterized as comprising less than about 2% by weight nicotine (e.g., less than about 1% by weight nicotine).

BRIEF DESCRIPTION OF THE DRAWINGS

In order to provide an understanding of embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION OF THE PREFERRED EMBODIMENTS

Figure 1:
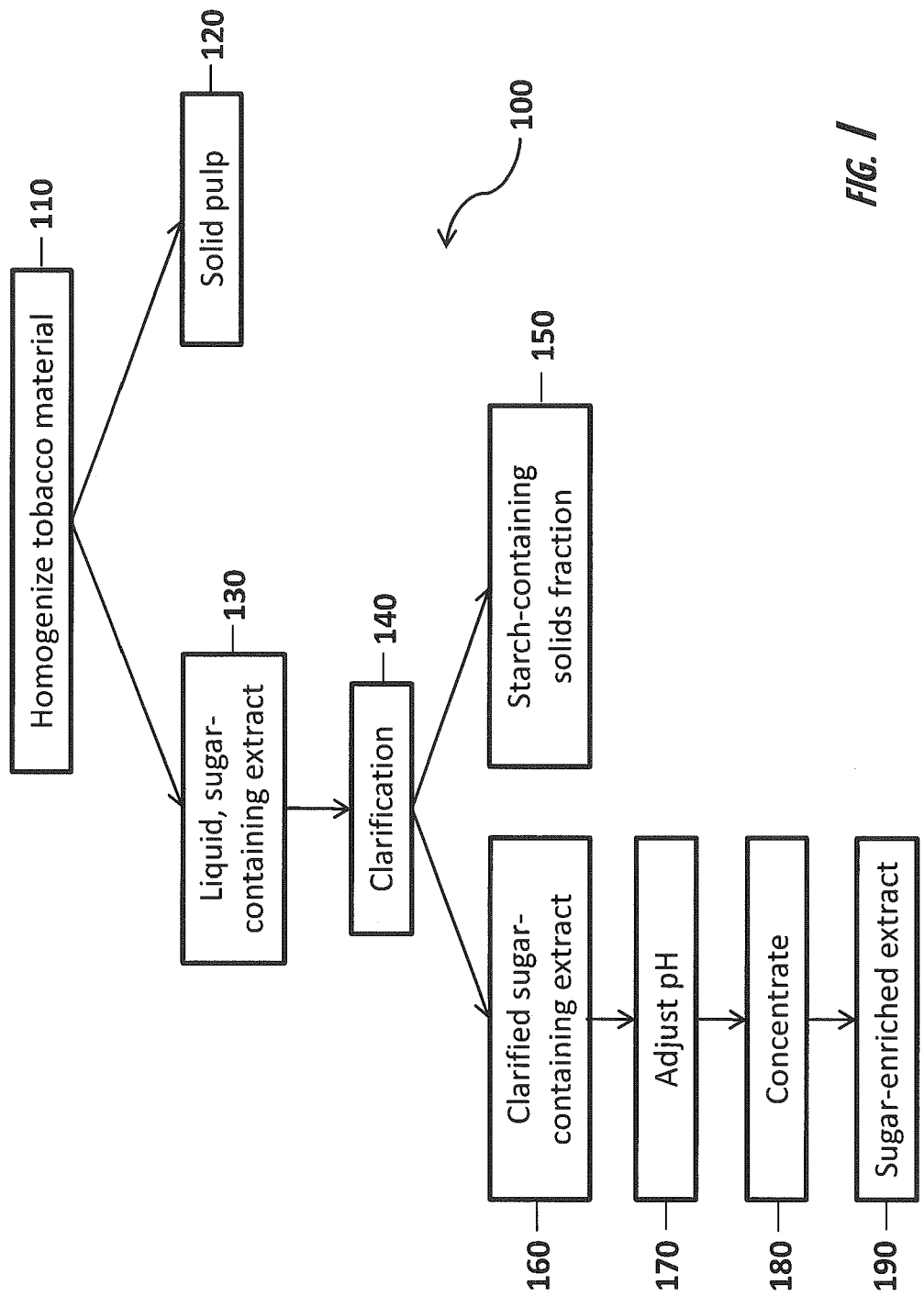
FIG. 1 is a schematic of one process embodiment for the derivation of sugars from a tobacco material.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water).

The present disclosure provides processes for isolating, separating, or otherwise extracting various components from a biomass such as a plant material (e.g., tobacco). In some embodiments, the processes can be tailored to extraction of specific components or may be generalized to extraction of components based on solubilities, compound type, compound chemical properties, compound physical properties, or the like. Exemplary components for extraction according to process described herein include, but are not limited to, starches, sugars and combinations thereof.

According to certain embodiments of the present disclosure, processes for obtaining a sugar-enriched extract from tobacco are provided. The types of sugars obtained from tobacco can vary. "Sugar" as used herein refers to carbohydrates including monosaccharides, having the general formula $(CH_2O)_n$, wherein n is an integer larger than two (e.g., fructose and glucose), disaccharides (e.g., lactose, maltose, and sucrose), oligosaccharides, and polysaccharides, which are oligomeric and polymeric compounds, respectively, comprising monosaccharides.

According to the present invention, sugar can be obtained from tobacco in various ways. For example, in some embodiments, a sugar-enriched extract is directly isolated from tobacco (e.g., by methods comprising extraction, as detailed herein). In some embodiments, a sugar-enriched extract is obtained by isolating starch and converting the starch to sugar. Advantageously, these methods can, in some embodiments, be combined such that the overall yield of sugar from a given tobacco sample is maximized.

The sugar-enriched extract obtained from tobacco as described herein generally comprise glucose and fructose, although other types of sugars may, in some embodiments, be included in the sugars obtained from tobacco. In certain embodiments, the sugars obtained from tobacco according to the methods provided herein substantially comprise glucose and fructose. For example, in certain embodiments, the sugar-enriched extract obtained from tobacco according to the methods described herein are at least about 90% glucose and fructose by weight of the sugars, at least about 92% glucose and fructose by weight of the sugars, at least about 95% glucose and fructose by weight of the sugars, at least about 98% glucose and fructose by weight of the sugars, or at least about 99% glucose and fructose by weight of the sugars (including about 100% glucose and fructose by weight of the sugars).

"High-fructose" typically refers to compositions wherein about 42% or more of the sugars are fructose. High fructose compositions generally have a sweet taste and one exemplary high fructose sugar composition is high-fructose corn syrup (HFCS), which is commonly used in processed foods and beverages, e.g., breads, cereals, lunch meats, yogurts, soups, and condiments. HFCS is obtained from corn and is generally provided by adding enzymes to a glucose-rich syrup derived from corn starch to convert some percentage of the glucose into fructose. Various grades of HFCS are available, including HFCS 42 (wherein the sugars comprise approximately 42% fructose and 53% glucose), HFCS 55 (wherein the sugars comprise approximately 55% fructose and 42% glucose), and HFCS 90 (wherein the sugars comprise approximately 90% fructose and 10% glucose). As used herein, "majority fructose" refers to compositions wherein more than about 50% by weight of the sugars in the composition comprise fructose.

The ratio of glucose to fructose in the sugar-enriched extract obtained from tobacco according to the disclosure can vary. In some embodiments, sugars directly obtained from tobacco comprise some percentage of fructose. For example, in some embodiments, a sugar-enriched extract directly obtained from tobacco (i.e., without any further treatment intended to change the sugar ratios) can comprise at least about 20% fructose, at least about 30% fructose, at least about 40% fructose, at least about 50% fructose, or at least about 60% fructose by weight. Advantageously, a sugar-enriched extract directly obtained from a tobacco material can comprise at least about 50% fructose by weight. In other words, in some embodiments, the sugar-enriched extract obtained from tobacco comprises more fructose than glucose. Accordingly, a high-fructose sugar material may, in some embodiments, be directly obtained from tobacco (i.e., without requiring any treatment intended to change the sugar ratios, e.g., enzymatic treatment to convert glucose to fructose). In other embodiments, the glucose to fructose weight ratio can be less than 1:1. In other words, in some embodiments, the sugar-enriched extract can comprise more glucose than fructose. In such embodiments, treatment (e.g., enzymatic treatment) may be conducted, if desired, to convert some portion of the glucose to fructose, e.g., to obtain a high-fructose tobacco-derived sugar material.

The present disclosure is applicable, in some embodiments, for large scale production, where the term large scale production refers to processing large quantities of a biomass (e.g., tobacco) on a mass production level. The term "biomass" and related terms such as "biomatter" and "plant source" are understood to refer to any portion of a harvested plant that may be processed to extract, separate, or isolate components of interest therefrom. The processing may be carried out in relation to various plants or portions thereof, such as seeds, flowers, stalks, stems, roots, tubers, leaves, or any further portions of the plant.

Exemplary tobacco plant materials used in accordance with the present disclosure may be of some form of a plant of the *Nicotiana* species. The selection of the plant from the *Nicotiana* species can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. *Nicotiana* species can be derived using genetic-modification or crossbreeding techniques (e.g., tobacco plants can be genetically engineered or crossbred to increase or decrease production of or to other change certain components, characteristics or attributes). Additional information on types of *Nicotiana* species suitable for use in the present invention can be found in US Pat. Appl. Pub. No. 2012/0192880 to Dube et al., which is incorporated by reference herein. Tobacco plants can be grown in greenhouses, growth chambers, or outdoors in fields, or grown hydroponically.

The *Nicotiana* species can be selected for the content of various compounds that are present therein. For example, plants can be selected on the basis that those plants produce relatively high quantities of one or more of the compounds desired to be isolated therefrom (e.g., sugars and/or starches). In certain embodiments, plants of the *Nicotiana* species (e.g., *Galpao commun* tobacco) are specifically grown for their abundance of leaf surface compounds.

The portion or portions of the plant of the *Nicotiana* species used according to the present invention can vary. For example, virtually all of the plant (e.g., the whole plant) can be harvested, and employed as such. Alternatively, various parts or pieces of the plant can be harvested or separated for further use after harvest. For example, the leaves, stem, stalk, roots, lamina, flowers, seed, and various portions and combinations thereof, can be isolated for further use or treatment. The plant material of the invention may thus comprise an entire plant or any portion of a plant of the *Nicotiana* species. See, for example, the portions of tobacco plants set forth in US Pat. Appl. Pub. Nos. 2011/0174323 to Coleman, III et al. and 2012/0192880 to Dube et al., which are incorporated by reference herein.

The plant of the *Nicotiana* species can be employed in either an immature or mature form, and can be used in either a green form or a cured form, as described in 2012/0192880 to Dube et al., which is incorporated by reference herein.

The tobacco material can be subjected to various treatment processes such as, refrigeration, freezing, drying (e.g., freeze-drying or spray-drying), irradiation, yellowing, heating, cooking (e.g., roasting, frying or boiling), fermentation, bleaching or otherwise subjected to storage or treatment for later use. In some embodiments, harvested tobacco can be sprayed with a buffer (e.g., a sodium metabisulfite buffer) to prevent the green plants from browning prior to further treatment as described herein. Other exemplary processing techniques are described, for example, in US Pat. Appl. Pub. Nos. 2009/0025739 to Brinkley et al. and 2011/0174323 to Coleman, III et al., which are incorporated by reference herein. At least a portion of the plant of the *Nicotiana* species can be treated with enzymes and/or probiotics before or after harvest, as discussed in U.S. patent application Ser. No. 13/444,272 to Marshall et al., filed on Apr. 11, 2012 and U.S. patent application Ser. No. 13/553,222 to Moldoveanu, filed on Jul. 19, 2012, which are incorporated herein by reference.

A harvested portion or portions of the plant of the *Nicotiana* species can be physically processed. A portion or portions of the plant can be separated into individual parts or pieces (e.g., roots can be removed from stalks, stems can be removed from stalks, leaves can be removed from stalks and/or stems, petals can be removed from the remaining portion of the flower). Although any single part of the tobacco plant or multiple parts of the tobacco plant can be used according to the present invention, preferably tobacco stalk, tobacco leaves, or both tobacco stalk and leaves are used. The harvested portion or portions of the plant can be further subdivided into parts or pieces (e.g., shredded, cut, comminuted, pulverized, milled or ground into pieces or parts that can be characterized as filler-type pieces, granules, particulates or fine powders). The harvested portion or portions of the plant can be subjected to external forces or pressure (e.g., by being pressed or subjected to roll treatment). For example, in certain embodiments, tobacco stalk, either alone or in combination with other portions of the plant (e.g., stalk and leaf together) can be used and may, in some embodiments, be subjected to the types of treatment described in US Pat. Appl. Publ. No. 2012/0152265 to Dube et al., which is incorporated herein by reference.

When carrying out such processing conditions, the harvested portion or portions of the plant can have a moisture content that approximates its natural moisture content (e.g., its moisture content immediately upon harvest), a moisture content achieved by adding moisture to the harvested portion or portions of the plant, or a moisture content that results from the drying of the harvested portion or portions of the plant. As such, harvested portion or portions of the plant can be used as such as components of tobacco products, or processed further.

According to the present invention, a portion or portions of a plant of the *Nicotiana* species are treated so as to provide one or more components (e.g., sugars) contained therein in a more usable (e.g., more concentrated) form. Various compounds or mixtures of compounds from the *Nicotiana* plant or portions thereof can be extracted and/or isolated by the methods provided herein. As used herein, an "isolated component," or "plant isolate," is a compound or complex mixture of compounds separated from a plant of the *Nicotiana* species or a portion thereof. The isolated component can be a single compound, a homologous mixture of similar compounds (e.g., isomers of a compound), or a heterologous mixture of dissimilar compounds (e.g., a complex mixture of various compounds of different types). See, for example, the description of isolated tobacco components and techniques for isolation in US Pat. Appl. Pub. Nos. 2007/0137663 to Taylor et al.; 2011/0174323 to Coleman, III et al.; 2011/0259353 to Coleman, III et al.; 2012/0141648 to Morton et al.; 2012/0192880 to Dube et al.; 2012/0192882 to Dube et al.; 2012/0272976 to Byrd et al., 2012/0211016 to Byrd, Jr. et al., and U.S. patent application Ser. No. 13/647,670 to Gerardi et al., which are incorporated by reference herein.

An illustration of an exemplary set of processing steps that can be carried out to obtain a sugar-enriched extract from a tobacco plant or portion thereof according to one embodiment of the invention is presented in FIG. 1. The specific sequence of steps illustrated in FIG. 1 should not be construed as limiting of the invention. Any modifications to the present disclosure which are functionally equivalent to the procedures and conditions disclosed herein are within the scope of the instant invention. For example, typical separation processes can include one or more process steps such as solvent extraction (e.g., using polar solvents, organic solvents, or supercritical fluids), chromatography (e.g., preparative liquid chromatography), clarification, distillation, filtration (e.g., ultrafiltration), recrystallization, and/or solvent-solvent partitioning. In some embodiments, the tobacco plant or portion thereof can be pre-treated, e.g., to liberate certain compounds to make the desired compounds available for more efficient separation. In some embodiments, multiple methods are used to obtain the desired compounds.

The process illustrated in FIG. 1 can be viewed in some embodiments as comprising a process 100 that can be carried out to obtain certain sugars from tobacco plants or portions thereof. In certain embodiments, the process according to the present invention can be viewed as a holistic plant component isolation and extraction process because the individual process steps provide for isolation or extraction of specifically desired plant components in a manner that does not preclude isolation or extraction of any other plant component in the same batch. For exemplary details on certain specific types of processing that can be conducted, see US Pat. App. Publ. No. 2012/0141648 to Morton et al.

As shown in the embodiment illustrated in FIG. 1, a tobacco material can be homogenized (110) to provide a solid pulp 120 and a liquid, sugar-containing extract 130. Extract 130 is clarified (140) to remove additional solids therefrom, giving a starch-containing solids fraction 150 and a clarified sugar-containing extract 160. Extract 160 is pH-adjusted (170) and concentrated (180) to give a sugar-enriched extract 190.

The homogenizing step 110 involves any type of processing of a plant material that is effective to break down the plant material and release component parts thereof. Specifically, homogenizing can refer to any processing that is effective to disrupt or break apart plant cell walls and release fluid and other materials contained within the plant cells. Such processing can include the use of an apparatus, such as a grinder, extruder, hammer mill, colloid mill, French press, or the like, as described in more detail in US Pat. Appl. Publ. 2012/0141648 to Morton et al., which is incorporated herein by reference.

Homogenizing step 110 may be performed, in some embodiments, in the presence of an extraction solvent. In this regard, the plant material may be subjected to a combined grinding and extraction process that subjects the plant material to a grinding action and simultaneously contacts the plant material with the extraction solvent. Alternatively, the homogenizing step may be conducted and subsequently, the ground material can be contacted with the extraction solvent. Thus, the plant material may be combined with the extraction solvent prior to, during, or after grinding.

Exemplary techniques useful for extracting components from *Nicotiana* species are described or referenced in US Pat. Appl. Pub. Nos. 2011/0259353 to Coleman, III et al. and 2012/0211016 to Byrd, Jr. et al., which are incorporated by reference herein. The extraction solvent for the extraction of sugars from tobacco according to the methods provided herein is preferably water (i.e., an aqueous solvent). Other exemplary extraction and separation solvents or carriers include alcohols (e.g., methanol or ethanol), hydrocarbons (e.g., heptane and hexane), diethyl ether, methylene chloride, supercritical carbon dioxide, and combinations thereof.

In some embodiments, the solvent may include any one or more of a variety of compounds useful to facilitate extraction of one or more specific components from the plant material. For example, in some embodiments, the extraction solvent may comprise one or more materials selected from the group consisting of co-solvents, detergents, surfactants, antioxidants, amino acids, buffers, protein extraction agents, enzymes, mineral acids, and combinations thereof. In some embodiments, the extraction solvent may comprise: glycine, one or more salts of phosphoric acid (e.g., as buffer materials), one or more bisulfite or metabisulfite containing compounds, one or more Group I or Group II halide salts (including NaCl, e.g., as protein extraction agents), and/or an antioxidant compound (e.g., ascorbic acid or a bisulfite or metabisulfite containing compound such as sodium metabisulfite ($Na_2S_2O_5$) or sodium bisulfate). In some embodiments, the extraction solvent may comprise a buffer solution that can be particularly useful to maintain or otherwise adjust the pH of the plant liquid component during the homogenizing step to a predetermined constant level. Because of the intimate mixing occurring during homogenization in the presence of the extraction solvent, it is understood that the plant liquid component can comprise not only the liquid components from the plant material but also some amount of the extraction solvent. When the extraction solvent functions as a buffer solution, it can be useful for the extraction solvent to include one or more neutralizing agents such as, for example, sodium phosphate.

According to some embodiments, the pH of the extraction solvent may be adjusted so as to maximize the amount of a specific plant component (e.g., starch or sugar) in the liquid, sugar-containing extract. For example, it may be useful to maintain the pH in the range of about 6.5 to about 8.0 in certain embodiments. Such a range specifically can be useful in relation to embodiments wherein it is desirable to maximize the starch content of the liquid, sugar-containing extract. In particular embodiments, the pH may be maintained at about 6.8 to about 7.6, particularly about 7.0 to about 7.4, and more particularly about 7.2. In some embodiments, it may be desirable to minimize the addition of excipients during the extraction and sugar extraction efficiency may be sufficient at neutral pH (i.e., around 7). In some embodiments, the efficiency of the sugar extraction may be slightly increased at a somewhat higher pH (i.e., within a pH range of about 6.5 to about 11, e.g., between about 8 and about 10.5).

The extraction solvent preferably can be combined with the plant material in specific ratios to achieve extraction of the desired components. In some embodiments, the extraction solvent and the plant material may be combined at a ratio of about 0.1 L to about 5 L of extraction solvent per 1 kg of biomass. In other embodiments, the ratio may be about 0.1 L to about 4 L, about 0.1 to about 3 L, about 0.1 to about 2 L, about 0.1 to about 1 L, about 0.2 L to about 0.8 L, about 0.3 L to about 0.7 L, or about 0.4 L to about 0.6 L of extraction solvent per 1 kg of biomass. In further embodiments, the process may use at least about 0.1 L, at least about 0.2 L, at least about 0.3 L, or at least about 0.4 L of extraction solvent per 1 kg of biomass. In one embodiment, the process can comprise combining about 0.5 L of extraction solvent per 1 kg or biomass.

The conditions of the extraction process can vary. In some embodiments, the plant of the *Nicotiana* species is combined with a solvent to form a material (e.g., in the form of a suspension or slurry). In certain embodiments, the amount of solvent added to form the moist material can be at least about 50 weight percent, or at least about 60 weight percent, or at least about 70 weight percent, based on the total weight of the material. In some cases, the amount of solvent can be described as at least about 80 weight percent or at least about 90 weight percent.

The resulting material can, in some embodiments, be heated at various temperatures and pressures. In certain embodiments, the material is heated to elevated temperatures (e.g., above room temperature) to effect extraction of compounds in the particulate material. For example, the moist material can be heated to greater than about 50° C., greater than about 60° C., greater than about 70° C., greater than about 80° C., greater than about 90° C., greater than about 100° C., greater than about 125° C., greater than about 150° C., greater than about 175° C., or greater than about 200° C. In certain embodiments, the pressure and temperature are adjusted such that the temperature of the moist material is elevated compared to the boiling point of water (or other solvent) at atmospheric pressure. One of skill in the art will be aware that the boiling point of a liquid is related to its pressure, and therefore will be able to adjust the pressure and temperature accordingly to cause boiling of the material.

The heating can be conducted in a pressure-controlled and pressurized environment, although atmospheric pressure in a vented tank can be used without departing from the invention. Preferred pressure vessels are equipped with an external heating source, and can also be equipped with means for agitation, such as an impeller. In other embodiments, the heat treatment process is conducted using an enclosed container placed in a microwave oven, a convection oven, or heated by infrared heating. Examples of vessels that provide a pressure-controlled environment are set forth in US Pat. Appl. Pub. No. 2012/0192880 to Dube et al., which is incorporated by reference herein. Typical pressures experienced by the reaction mixture during the heating process often range from about 10 psig to about 1,000 psig, normally from about 20 psig to about 500 psig.

The heating step can be conducted in atmospheric air, or ambient atmosphere or within a controlled atmosphere, such as a generally inert atmosphere. Gases such as nitrogen, argon and carbon dioxide can be used. Alternatively, a hydrocarbon gas (e.g., methane, ethane or butane) or a fluorocarbon gas also can provide at least a portion of a controlled atmosphere in certain embodiments, depending on the choice of treatment conditions and desired reaction products.

The amount of time required to effectuate extraction is partially dependent on the temperature and pressure at which the extraction is conducted. For example, in some embodiments, heating the material to an elevated temperature and/or pressurizing the material increases the rate of extraction. The time range for the extraction process is typically at least about 30 minutes (e.g., at least about 1 hour or at least about 2 hours) and typically less than about 24 hours (e.g., less than about 12 hours or less than about 8 hours), although other time periods could be used without departing from the invention. In some embodiments, multiple extractions can be conducted to extract additional compounds therefrom. See, for example, US Patent App. Publ. No. 2008/0254149 to Havkin-Frenkel, which is incorporated herein by reference.

After the tobacco material is homogenized, the resulting material can be separated into a solid pulp 120 and a liquid, sugar-containing extract 130 (i.e., the liquid extracted from the processed plant material according to the present disclosure). The separating can be done by any means, e.g., a rough filtration or other method for withdrawal of the liquid component from the homogenized mixture. For example, a screw press can be used to separate these components. The solid pulp 120 generally contains primarily plant fiber (or cellulose) and pectin and can, in some embodiments, be separately processed as provided in US Pat. Appl. Pub. 2012/0141648 to Morton et al., which is incorporated herein by reference.

The liquid, sugar-containing extract 130 can, in various embodiments, be in the form of a green or brown juice; however, it should be understood that the term "liquid, sugar-containing extract" may refer to any liquid extracted from a plant material or biomatter, regardless of the extracted liquid's color. Extract 130 may, in some embodiments, comprise components including, but not limited to, proteins, peptides, sugars, and/or alkaloids. The liquid, sugar-containing extract typically comprises some level of solid (insoluble) material entrained in the liquid. The extract may be characterized as being a slurry, suspension, or solution, depending upon the specific embodiment, which can be determined based upon the type of plant material used, the specific extraction solvent used, and the component desired for isolation.

Following homogenization and separation from solid pulp 120, the sugar-containing extract 130 can be processed to clarify the juice as illustrated by step 140 of FIG. 1. Clarification generally results in the removal of some or all of the portion of the plant material that is insoluble in the extraction solvent of the sugar-containing extract. In some embodiments, clarification can result in the removal of additional high-molecular weight components of extract 130. The clarification step provides a solids fraction 150 and a clarified sugar-containing extract 160. Clarification can be an important step in achieving a desired concentration of certain desired plant components (e.g., starch) in the insoluble fraction and/or a desired concentration of certain desired plant components (e.g., sugars) in the soluble fraction. See, for example, the clarification techniques set forth in US Patent App. Publ. No. 2012/0152265 to Dube et al., which is incorporated by reference herein.

In certain embodiments, clarification comprises multiple steps, including, but not limited to, one or more chemical treatment steps, one or more heating steps, one or more filtration steps, one or more other types of separation steps (e.g., centrifugation and/or sedimentation), or some combination thereof. Where clarification comprises multiple steps, it is to be understood that these multiple steps can be conducted in any order.

Clarification step 140 can, in some embodiments, involve the addition of various materials (i.e., clarifying agents) to an extracted liquid. For example, specific clarifying agents that may be added to the raw, extracted liquid include, but are not limited to, various salts, lime, sulfur, and other compounds to stabilize or clarify the liquid. In certain embodiments, the pH of the extract can be modified, e.g., via the addition of a suitable amount of an acid or base. Exemplary acidic or basic materials useful for this purpose include, but are not limited to, hydrochloric acid, phosphoric acid, and/or sodium hydroxide. In certain embodiments, the pH of extract 130 is adjusted to a value of about 7.

In some embodiments, adjusting the pH of the extract can stabilize or clarify the liquid. In some embodiments, adjusting the pH of the extract can facilitate precipitation of specific components (desirable or undesirable) therefrom, which can subsequently be removed.

In some embodiments, added clarifying agents can function as flocculants, which can facilitate the removal of one or more impurities. For example, flocculants and/or filter aids may remove suspended particles and/or dissolved molecules or ions. Some common exemplary filter aids include cellulose fibers, perlite, bentonite, diatomaceous earth ("DE"), and other silaceous materials. The flocculant and/or filter aids can subsequently be removed from the liquid by any means (e.g., filtration, settling, centrifugation, etc.).

In certain embodiments, clarification step 140 comprises heating the extract. In some embodiments, the liquid can, be heated to initiate the desired reactions for clarification and/or to solubilize or unsolubilize certain components of the extract. The temperature and time for which the extract is heated can vary. In some embodiments, extract 130 is heated to boiling, which may result in the formation of additional solids, which can subsequently be removed by any of the methods described herein. In some embodiments, it may be desirable to heat the extract to remove some of the solvent (i.e., to concentrate the extract). For example, in one embodiment, the extracted liquid can be heated in a vented vessel to evaporate a portion of the water. The temperature and pressure at which the liquid is heated may vary. See, for example, the solvent removal techniques set forth in US Pat. Pub. No. 2012/0152265 to Dube et al., which is incorporated by reference herein.

In some embodiments, clarifying step 140 comprises introducing the sugar-containing extract 130 into a separating apparatus, such as a centrifuge (e.g., a decanter centrifuge). The extract can be centrifuged to separate the extract into a soluble liquid fraction (permeate) (i.e., clarified, sugar-containing extract 160) and a solids fraction 150. Representative centrifuge systems are described in, for example, U.S. Pat. No. 6,817,970 to Berit et al., U.S. Pat. No. 5,899,845 to Kohlstette et al., U.S. Pat. No. 5,267,937 to Zettier et al., U.S. Pat. No. 4,966,576 to Schulz et al., and U.S. Pat. No. 5,865,719 to Droste et al., each of which is incorporated herein by reference in its entirety. Suitable conditions for centrifugation may be based, for example, upon time interval, feed rate, dwell time for expulsion of solid pellet material, operation speed, and G-force.

In some embodiments, clarifying step 140 comprises filtering sugar-containing extract 130. The process of filtration can comprise passing the liquid through one or more filter screens and/or membranes to remove selected sizes of particulate matter (giving a retentate that remains on or in the filter material and a permeate that passes through the filter material) and/or components of the extract having a molecular weight above a certain threshold. Screens may be, for example, stationary, vibrating, rotary, or any combination thereof. Filters may be, for example, press filters or pressure filters. In some embodiments, the filtration method used can involve microfiltration, ultrafiltration, and/or nanofiltration. To remove solid components, alternative methods can also be used, for example, centrifugation or settling/sedimentation of the components and siphoning off of the liquid, or any combination of the techniques noted herein.

In some embodiments, ultrafiltration is employed, wherein the material to be filtered is brought into contact with a semipermeable membrane. The membrane can be of any type, such as plate-and-frame (having a stack of membranes and support plates), spiral-wound (having consecutive layers of membrane and support material rolled up around a tube), tubular (having a membrane-defined core through which the feed flows and an outer, tubular housing where permeate is collected), or hollow fiber (having several small diameter tubes or fibers wherein the permeate is collected in the cartridge area surrounding the fibers). The membrane can be constructed of any material. For example, polysulfone, polyethersulfone, polypropylene, polyvinylidenefluoride, and cellulose acetate membranes are commonly used, although other materials can be used without departing from the invention described herein. See, for example, the ultrafiltration techniques set forth in US Patent App. Publ. No. 2012/0152265 to Dube et al., which is incorporated by reference herein.

Ultrafiltration membranes are available in a wide range of pore sizes (typically ranging from about 0.1 to about 0.001 microns). Membranes are more typically described by their molecular weight cutoffs. Ultrafiltration membranes are commonly classified as membranes with number average molecular weight cutoffs of from about $10^3$ Da to about $10^5$ Da. In practice, compounds with molecular weights above the molecular weight cutoff are retained in the retentate, and the compounds with molecular weights below the cutoff pass through the filter into the permeate. Ultrafiltration methods typically are not capable of removing low molecular weight organic compounds and ions.

Ultrafiltration is typically a cross-flow separation process. The liquid stream to be treated (feed) flows tangentially along the membrane surface, separating into one stream that passes through the membrane (permeate) and another that does not (retentate or concentrate). The operating parameters of the ultrafiltration system can be varied to achieve the desired result. For example, the feed mixture to be filtered can be brought into contact with the membrane by way of applied pressure. The rate of permeation across the membrane is directly proportional to the applied pressure; however, the maximum pressure may be limited. The flow velocity of the mixture across the membrane surface can be adjusted. Temperature can also be varied. Typically, permeation rates increase with increasing temperature.

Commercial ultrafiltration systems are readily available and may be used for the ultrafiltration methods of the present invention. For example, commercial suppliers such as Millipore, Spectrum® Labs, Pall Corporation, Whatman®, Porex Corporation, and Snyder Filtration manufacture various filter membranes and cartridges, and/or filtration systems (e.g., tangential flow filtration systems). Exemplary membranes include, but are not limited to, Biomax® and Ultracel® membranes and Pellicon® XL cassettes (from Millipore), Microkros®, Minikros®, and KrosFlo® Hollow Fiber Modules (from Spectrum® Labs), and Microza filters and Centramate,™ Centrasette,™ Maximate™, and Maxisette™ Tangential Flow Filtration Membrane Cassettes. Commercially available filtration systems include, but are not limited to, Millipore's Labscale™ Tangential Flow Filtration (TFF) system and Spectrum® Labs' KrosFlo® and MiniKros® Tangential Flow Filtration Systems.

Filters and/or membranes that may be useful according to the present invention include those with molecular weight cutoffs of less than about 100,000 Da, less than about 75,000 Da, less than about 50,000 Da, less than about 25,000 Da, less than about 20,000 Da, less than about 15,000 Da, less than about 10,000 Da, and less than about 5,000 Da. In certain embodiments, a multistage filtration process is used. Such embodiments employ multiple filters and/or membranes of different (typically decreasing) molecular weight cutoffs. Any number of filters and/or membranes can be used in succession according to the invention. For example, a first filtration may be conducted using a 50,000 Da molecular weight cutoff filter and a second filtration may be conducted using a 5,000 Da molecular weight cutoff filter. In certain embodiments, the filtration step employs ceramic microfilters, such as those having filter sizes of 0.5 µm or less, 0.4 µm or less, 0.3 µm or less, 0.2 µm or less, or 0.1 µm or less. Further filtration means suitable for use in the various embodiments of the invention where filtration is desirable include those disclosed in U.S. Pat. No. 4,941,484 to Clapp et al., the disclosure of which is incorporated herein by reference in its entirety.

Clarification can, in certain embodiments, result in some degree of concentration of the liquid component of the sugar-containing extract. The degree of concentration can vary, depending upon the specific steps comprising the clarification process.

Following clarification, the pH of the clarified sugar-containing extract 160 is typically adjusted (step 170 of FIG. 1). The pH of the liquid concentrate may be adjusted by addition of a suitable amount of an acidic or basic material, such as hydrochloric acid, phosphoric acid, or sodium hydroxide. The desired pH can vary depending upon the desired final product. In some specific embodiments, the pH of the concentrated extract is adjusted to a value of at least about 8 or at least about 8.4. Although not intended to be limiting of the invention, it is believed that adjusting the pH to a value above about 8.4 advantageously causes nicotine to pass with water into the distillate in the final concentrating step. Consequently, the sugar can be concentrated in the retentate while the concentration of nicotine remains the same or, in some embodiments, is reduced.

The pH-adjusted retentate is then subjected to concentration (step 180 of FIG. 1) to provide a concentrated, sugar-enriched tobacco extract 190. The concentration step can be conducted to provide a sugar-enriched tobacco extract having a given total solids value. For example, in some embodiments, the retentate is concentrated to a total solids content of at least about 50%, at least about 60%, or at least about 70% by weight. The method of concentration can vary and any method capable of decreasing the amount of liquid and consequently concentrating the sugar in the extract can be used. For example, representative methods of solvent removal include heat treatment to evaporate the solvent, reverse osmosis membrane treatment, spray drying, or freeze drying. In certain embodiments, reverse osmosis and/or a vacuum evaporator can be used to provide the sugar-enriched tobacco extract 190. Varying temperatures and pressures can be used to accomplish this concentration step. Advantageously, the concentration step results in the removal of water and, in some embodiments, a substantial portion of the nicotine. For example, the sugar-enriched extract advantageously comprises less than about 2% nicotine by weight, less than about 1% nicotine by weight, or less than about 0.5% nicotine by weight. For example, the sugar-enriched extract can comprise between about 0.1% and about 2% nicotine by weight, between about 0.1% and about 1% nicotine by weight, or between about 0.1% and about 0.5% nicotine by weight.

In certain embodiments, the sugars present in the sugar-enriched extract 190 are at least about 90% glucose and fructose by weight of the sugars, at least about 92% glucose and fructose by weight of the sugars, at least about 95% glucose and fructose by weight of the sugars, at least about 98% glucose and fructose by weight of the sugars, or at least about 99% glucose and fructose by weight of the sugars present therein (including about 100% glucose and fructose by weight of the sugars). Surprisingly, the sugar-enriched extract in some embodiments exhibits a high fructose concentration. For example, in certain embodiments, the sugars present in the sugar-enriched extract comprise about 50% or more by weight of fructose. Typically, without treatment to convert glucose to fructose, most naturally occurring sugars obtained from various plants comprise a greater percentage of glucose than fructose. Of course, if an ever greater percentage of fructose is desired according to the present application, some percentage of the glucose in the sugar-enriched extract can be converted to fructose by means of an additional step (e.g., treatment with an isomerase).

Figure 2:
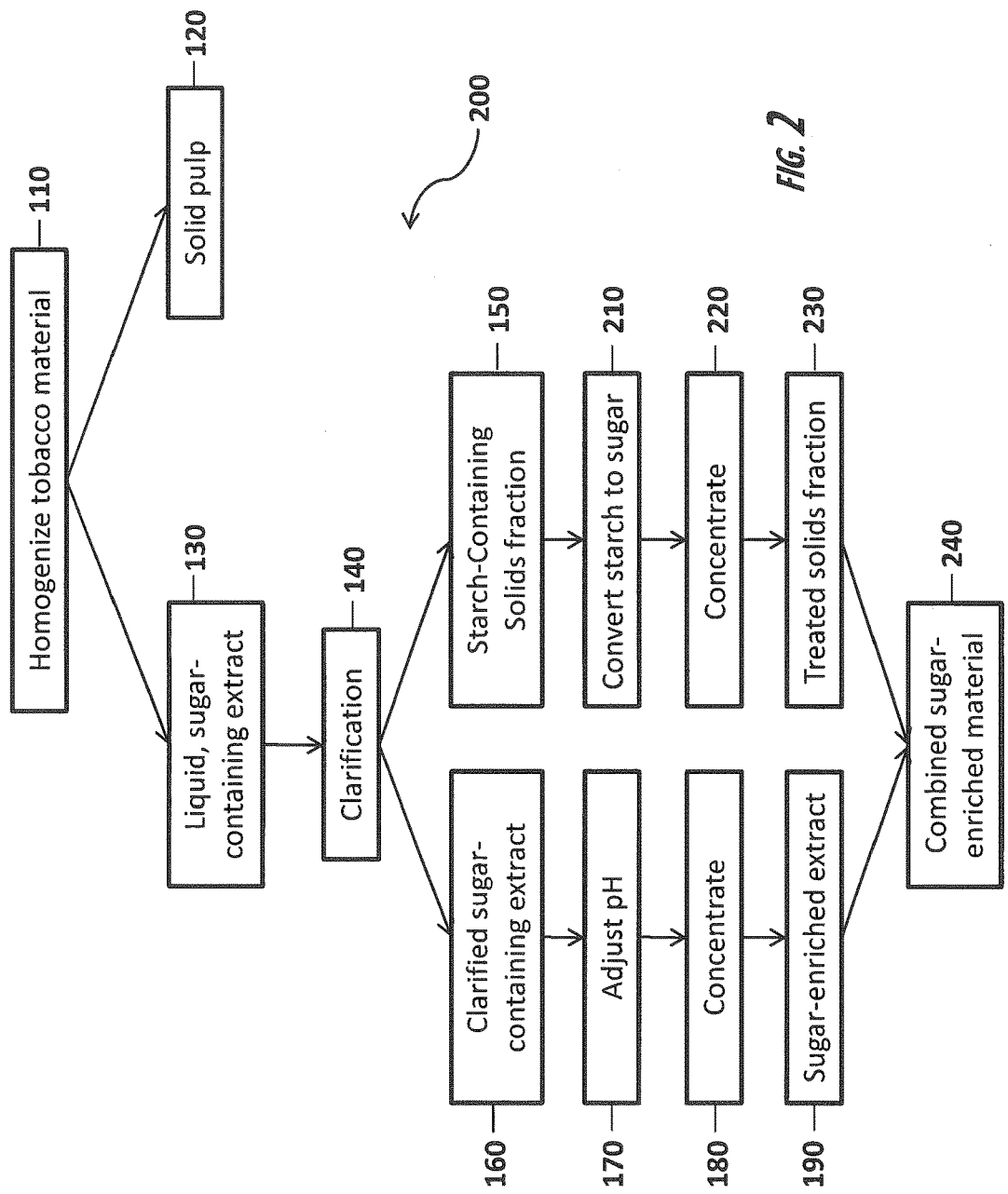
FIG. 2 is a schematic of a different process embodiment for the derivation of sugars from a tobacco material, which can be combined with the process of FIG. 1 as shown to increase the amount of sugars obtained from a tobacco material.

FIG. 2 provides an additional process 200 for obtaining sugars from a tobacco plant or portion thereof and combining such sugars with the sugar-enriched extract 190 obtained according to the method outlined above and illustrated in FIG. 1. The solids fraction 150 obtained from the clarification step 140 of FIG. 1 can in some embodiments be further processed to provide additional sugar. Typically, solids fraction 150 comprises some concentration of starch. In certain embodiments, the solids fraction can comprise at least about 40% by weight of starch on a dry weight basis. In further embodiments, the solids fraction can comprise at least about 50% starch by weight, at least about 60% starch by weight, or at least about 70% starch by weight on a dry weight basis. In still further embodiments, the solids fraction can comprise about 40% to about 95% starch by weight, about 50% to about 90% starch by weight, or about 60% to about 85% starch by weight, on a dry weight basis.

The solids fraction can be dried, for example, using an oven, vortex dryer, flash drying technology, spray drying, or any other suitable drying process to give a dried solid. The temperature at which the solids fraction is dried can vary and can be, for example, a temperature greater than room temperature, such as up to about 90° C., up to about 80° C., or up to about 70° C. In some embodiments, drying may be at a temperature of about 40° C. to about 90° C., about 50° C. to about 80° C., or about 60° C. to about 70° C. The solids fraction may be dried to a desired moisture content such as, for example, less than about 20% by weight, less than 15% by weight, or less than about 10% by weight. In some embodiments, the dried solids fraction can then be ground, milled, or otherwise pulverized to provide a powder or granular material.

The content of the dried solids fraction can vary; however, in certain embodiments, the dried solids fraction comprises a tobacco-derived starch material, i.e., a compound comprising one or more polysaccharides containing multiple monosaccharide units. In particular, the tobacco-derived starch can be a polymer containing a plurality of glucose molecules connected by hydrolysable alpha linkages (i.e., alpha-1,4-glucosidic linkages). The number average molecular weight of the starch can vary, but typically can be up to about 50,000 Da, up to about 40,000 Da, up to about 30,000 Da, or up to about 20,000 Da. In other embodiments, the number average molecular weight of the starch can be about 500 Da to about 30,000 Da, about 1,000 Da to about 20,000 Da, or about 2,000 Da to about 10,000 Da.

In some embodiments, the solids fraction can be further processed, e.g., by extraction to provide a purer tobacco-derived starch material. Exemplary methods for such further processing are provided, for example, in US Pat. Appl. Publ. No. 2012/0141648 to Morton et al., which is incorporated herein by reference.

The dried solids fraction in certain embodiments of the invention is processed (step 210) to convert at least a portion of the starch contained therein to sugars. This conversion step can be accomplished in various ways. In some embodiments, the starch-containing solids fraction 150 is first boiled in water to begin to break down the starch molecules. In certain embodiments, the boiling step is conducted at an acidic pH. For example, the pH of the solution can be below about 7, below about 6, below about 5, below about 4, below about 3, or below about 2. In one exemplary embodiment, the boiling is conducted at a pH of about 1.8.

In some embodiments, conversion step 210 comprises contacting the starch-containing solids fraction 150 with one or more enzymes. The amount of enzyme added can vary and may range from about 0.01% by volume of the solids fraction to about 5% by volume (e.g., between about 0.05% and about 1%, e.g., between about 0.1% and about 0.5%), although more or less enzyme can be used in various embodiments without departing from the present invention. One exemplary enzyme commonly used to convert starch to sugar is α-amylase. Various types of α-amylase are known and can be used according to the methods provided herein. Generally, α-amylase can break down the α-1,4-glycosidic bond of starch molecules but not the α-1,6-glycosidic bond. The breakdown of the α-1,4-glycosidic bond of starch molecules yields molecules of branched, but short, glucose. Alternatively, or in addition, enzymes such as amyloglucosidase and/or xylose isomerase can be used for this purpose.

In some embodiments, the pH of the solids fraction is altered prior to conversion step 210 (e.g., enzyme treatment), such that the mixture has a pH of between about 5 and 6. For example, in one embodiment, the mixture is adjusted to a pH of about 5.5 prior to the addition of α-amylase. In one embodiment, the mixture is adjusted to a pH of about 5 prior to the addition of amyloglucosidase. Similarly, the temperature of the solids fraction can be altered for enzyme treatment. For example, the enzyme treatment can be conducted at elevated temperature (e.g., between about 20° C. and about 100° C., such as greater than about 20° C., greater than about 30° C., greater than about 40° C., greater than about 50° C., greater than about 60° C., greater than about 70° C., greater than about 80° C., or greater than about 90° C.). In certain embodiments, α-amylase treatment can be conducted at an elevated temperature, e.g., about 98° C. and amyloglucosidase treatment can be conducted at a relatively lower (but still elevated) temperature, e.g., about 37° C.

The time for which the enzyme remains in contact with the mixture can vary. For example, in some embodiments, the enzyme remains in contact with the mixture for at least about 5 minutes, at least about 15 minutes, at least about 30 minutes, at least about 1 hour, at least about 1.5 hours or at least about 2 hours. In some embodiments, the enzyme-containing mixture can be agitated for all or a portion of the treatment time.

The resulting, enzyme-treated material, comprising some concentration of sugar, is generally then filtered, e.g., to remove the enzymes. Enzymes can be removed, for example, by passing the enzyme-treated material through a 0.1 μm ceramic membrane. The enzymes will be isolated in the retentate and the permeate will comprise the sugars produced. The permeate can optionally be further treated, e.g., to remove any protein contained in the 0.1 μm permeate (e.g., on a 1 kDa filter). The permeate is then concentrated (220) and dried (e.g., as described herein) to give a treated solids fraction 230. The solid thus produced can optionally be further treated, e.g., to clarify the material, using any of the clarification techniques noted herein.

In some embodiments, the resulting treated solids fraction 230 provided according to the method herein described can be combined with the final sugar-enriched extract directly obtained from tobacco (e.g., according to the method shown in FIGS. 1-2). Although as depicted in FIG. 2, the final products of both steps are illustrated as being combined (i.e., treated solids fraction 230 is combined with sugar-enriched extract 190), it is noted that the sugar-containing materials can be combined at varying points in the process. For example, in certain embodiments, the treated solids fraction 230 can be independently prepared and combined with the extract-derived sugar material at any stage of the isolation of sugar from the clarified sugar-containing extract (e.g., at step 170 or step 180 or after step 180 of FIGS. 1-2). Similarly, in some embodiments, the concentrated sugar-containing material derived from the soluble fraction can be added in at any stage of the isolation of sugar from the solids fraction (e.g., at step 210, 220, or after step 220 of FIG. 2).

The overall yield of combined sugar-enriched material 240 from the combined process of FIG. 2 can vary. In certain embodiments, the combined process gives a glucose yield of at least about 20 g glucose per kg dried tobacco biomass (by dry weight), at least about 25 g glucose per kg dried tobacco biomass (by dry weight), or at least about 30 g glucose per kg dried biomass (by dried weight). In certain embodiments, the combined process further gives a fructose yield (in the absence of isoisomerase treatment to convert any of the glucose to fructose) of at least about 15 g fructose per kg dried biomass (by dried weight), at least about 20 g fructose per kg dried biomass (by dried weight), at least about 25 g fructose per kg dried biomass (by dried weight), or at least about 30 g fructose per kg dried biomass (by dried weight).

Although in some embodiments, the tobacco-derived material (e.g., sugar-enriched extract 190, treated solids fraction 230, or combined sugar-enriched material 240) is used directly, it may be desirable to thermally treat the tobacco-derived material in order to, for example, pasteurize the material or otherwise chemically alter the material. This thermal treatment can be conducted before or after any of the processes described herein (e.g., before or after any of the steps in process 100 of FIG. 1 and/or the steps in process 200 of FIG. 2) for the isolation of one or more components from a plant of the *Nicotiana* species. For example, a tobacco material can be thermally processed by mixing the tobacco material, water, and an additive selected from the group consisting of lysine, glycine, histidine, alanine, methionine, glutamic acid, aspartic acid, proline, phenylalanine, valine, arginine, di- and trivalent cations, asparaginase, saccharides, phenolic compounds, reducing agents, compounds having a free thiol group, oxidizing agents (e.g., hydrogen peroxide), oxidation catalysts, plant extracts, and combinations thereof, to form a moist tobacco mixture; and heating the moist tobacco mixture at a temperature of at least about 60° C. to form a heat-treated tobacco mixture. In one embodiment, the treated tobacco extract is heat treated in the presence of water, NaOH, and an additive (e.g., lysine) at about 88° C. for about 60 minutes. Such heat treatment can help prevent acrylamide production resulting from reaction of asparagine with reducing sugars in tobacco materials and can provide some degree of pasteurization. See, for example, US Pat. Pub. No. 2010/0300463 to Chen et al., which is incorporated herein by reference. In certain embodiments wherein a heat-treated tobacco-derived material is used in a smokeless tobacco product of the present invention, the product can be characterized by very low acrylamide content. For example, in some embodiments, the smokeless tobacco product is characterized by an acrylamide content of less than about 500 ppb (ng/g), less than about 400 ppb, less than about 300 ppb, less than about 200 ppb, or less than about 100 ppb.

Following one or more of the methods disclosed herein for the isolation of one or more components from a plant of the *Nicotiana* species, any liquid material thus obtained can be further processed if desired. For example, the tobacco material can be subjected to further treatment steps, which can be used in the place of, or in addition to, the other isolation steps described herein. In some embodiments, the extract (e.g., clarified extract 160, sugar-enriched extract 190, or combined material 240) is brought into contact with an imprinted polymer or non-imprinted polymer such as described, for example, in US Pat. Pub. Nos. 2007/0186940 to Bhattaeharyya et al; 2011/0041859 to Rees et al.; and 2011/0159160 to Jonsson et al; and U.S. patent application Ser. No. 13/111,330 to Byrd et al., filed May 19, 2011, all of which are incorporated herein by reference. Treatment with a molecularly imprinted or non-imprinted polymer can be used to remove certain components of the extract, such as tobacco-specific nitrosamines (TSNAs), including N'-nitrosonornicotine (NNN), (4-methylnitrosamino)-1-(3-pyridyl)-1-butanone (NNIS), N'-nitrosoanatabine (NAT), and N'-nitrosoanabasine (NAB); polyaromatic hydrocarbons (PAHs), including benz[a]anthracene, benzo[a]pyrene, benzo[b]fluoranthene, benzo[k]fluoranthene, chrysene, dibenz [a,h]anthracene, and indeno[1,2,3-cd]pyrene; or other Hoffmann analytes.

In some embodiments, one or more of the materials (e.g., extracts or solids) described herein can be subjected to conditions so as to cause compounds contained in such materials to undergo chemical transformation. For example, the tobacco material obtained from plants of the *Nicotiana* species or portion thereof can be treated to cause chemical transformation or be admixed with other ingredients. In some embodiments, the tobacco-derived extracts (including liquid and solids fractions) obtained therefrom can be treated to cause chemical transformation or be admixed with other ingredients. The chemical transformations or modification of the tobacco material or extract thereof can result in changes of certain chemical and physical properties of the tobacco material or extract (e.g., the sensory attributes thereof). Exemplary chemical modification processes can be carried out by acid/base reaction, hydrolysis, oxidation, heating and/or enzymatic treatments; and as such, compounds can undergo various degradation reactions. Exemplary chemical transformation techniques are set forth in US Pat. Appl. Pub. Nos. 2011/0174323 to Coleman, III, et al. and 2011/0259353 to Coleman, III et al., which are incorporated by reference herein.

In certain embodiments, the tobacco material or extract thereof (including liquid and/or solid fractions) is treated to provide degradation products. Degradation products are any compounds that are produced from the compounds extracted and/or isolated according to the present invention. Degradation products can be formed naturally from such compounds or may be produced by an accelerated degradation process (e.g., by the addition of heat and/or chemicals to accelerate the breakdown of the compounds). These compounds can be degraded, for example, by means of oxidation (e.g., through treatment with $H_2O_2$ or other oxidizing agents) and/or hydrolysis reactions.

The form of the sugar-enriched tobacco extract 190, treated solids fraction 230, and combined sugar-enriched material 240 obtained according to the present invention can vary. Typically, extract 190, solids fraction 230, and combined material 240 are in solid, liquid, or semi-solid or gel forms. The resulting formulations can be used in concrete, absolute, or neat form. Solid forms of the tobacco-derived materials described herein can include spray-dried and freeze-dried forms. Liquid forms of the tobacco-derived materials described herein can include formulations contained within aqueous or organic solvent carriers.

Sugar-enriched tobacco extracts 190, treated solids fractions 230, and combined sugar-enriched materials 240 are useful as materials for various compositions. For example, in some embodiments, the tobacco-derived materials described herein are incorporated within tobacco compositions, particularly tobacco compositions incorporated into smoking articles or smokeless tobacco products. In accordance with the present invention, a tobacco product incorporates tobacco that is combined with one or more of the tobacco-derived materials (e.g., extract 190, solids fraction 230, and/or combined sugar-enriched material 240) according to the invention. That is, a portion of the tobacco product can be comprised of some form of tobacco extract formulation prepared according to the invention.

Addition of the tobacco-derived material or materials described herein to a tobacco composition can enhance a tobacco composition in a variety of ways, depending on the nature of the tobacco-derived material and the type of tobacco composition. Exemplary extracts, solids fractions, and combinations thereof can serve to provide flavor and/or aroma to a tobacco product (e.g., the composition can alter the sensory characteristics of tobacco compositions or smoke derived therefrom). Other extracts, solids fractions, and combinations thereof can serve functional purposes within tobacco compositions, such as binder or filler functions. Certain extracts, solids fractions, and combinations thereof can serve as a replacement for one or more traditional components of a tobacco product.

The tobacco product to which the tobacco-derived materials of the present disclosure are added can vary, and may include any product configured or adapted to deliver tobacco or some component thereof to the user of the product. Exemplary tobacco products include smoking articles (e.g., cigarettes), smokeless tobacco products, and aerosol-generating devices that contain nicotine and/or a tobacco material or other plant material that is not combusted during use. The incorporation of the sugar-enriched, tobacco-derived materials of the invention into a tobacco product may involve use of a tobacco material or non-tobacco plant material as a carrier for the formulations, such as by absorbing the tobacco-derived, sugar-enriched material (e.g., extract 190, solids fraction 230, and/or combined sugar-enriched material 240) into the tobacco or other plant material or otherwise associating tobacco-derived, sugar-enriched material with the carrier material. The types of tobacco that can serve as the carrier for the formulations of the invention can vary, and can include any of the tobacco types discussed herein, including various cured tobacco materials (e.g., flue-cured or air-cured tobaccos) or portions thereof (e.g., tobacco lamina or tobacco stems). The physical configuration of the tobacco material to which the formulation is added can also vary, and can include tobacco materials in shredded or particulate folio, or in the form of a sheet (e.g., reconstituted tobacco sheets) or in whole leaf form.

Accordingly, sugar-enriched, tobacco-derived materials provided herein can, in some embodiments, be used as compositions in the manufacture of smoking articles. For example, the formulations prepared in accordance with the present invention can be mixed with casing materials and applied to tobacco as a casing ingredient or as a top dressing. Still further, the formulations of the invention can be incorporated into a cigarette filter (e.g., in the filter plug, plug wrap, or tipping paper) or incorporated into cigarette wrapping paper, preferably on the inside surface, during the cigarette manufacturing process. See, for example, the description and references related to tobacco isolates used in smoking articles set forth in US Pat. Pub. No. 2012/0192880 to Dube et al., which is incorporated by reference herein. Representative tobacco blends, non-tobacco components, and representative cigarettes manufactured therefrom are also set forth in the Dube et al. reference noted above.

Figure 3:
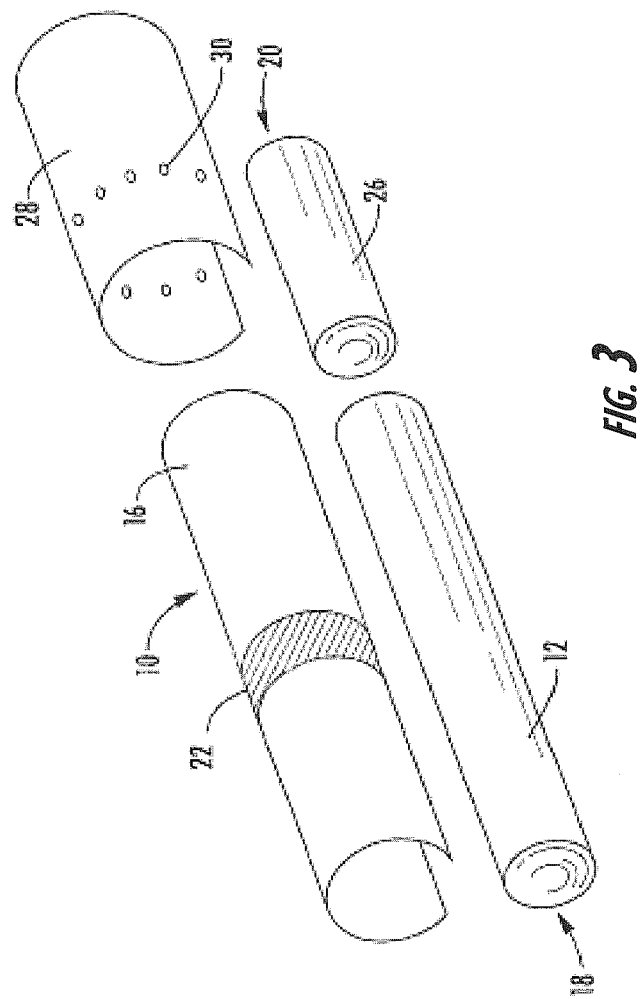
FIG. 3 is an exploded perspective view of a smoking article having the form of a cigarette, showing the smokable material, the wrapping material components, and the filter element of the cigarette.

Referring to FIG. 3, there is shown a smoking article 10 in the form of a cigarette and possessing certain representative components of a smoking article that can contain the formulation of the present invention. The cigarette 10 includes a generally cylindrical rod 12 of a charge or roll of smokable filler material (e.g., about 0.3 to about 1.0 g of smokable filler material such as tobacco material) contained in a circumscribing wrapping material 16. The rod 12 is conventionally referred to as a "tobacco rod." The ends of the tobacco rod 12 are open to expose the smokable filler material. The cigarette 10 is shown as having one optional band 22 (e.g., a printed coating including a film-forming agent, such as starch, ethylcellulose, or sodium alginate) applied to the wrapping material 16, and that band circumscribes the cigarette rod in a direction transverse to the longitudinal axis of the cigarette. The band 22 can be printed on the inner surface of the wrapping material (i.e., facing the smokable filler material), or less preferably, on the outer surface of the wrapping material.

At one end of the tobacco rod 12 is the lighting end 18, and at the mouth end 20 is positioned a filter element 26. The filter element 26 positioned adjacent one end of the tobacco rod 12 such that the filter element and tobacco rod are axially aligned in an end-to-end relationship, preferably abutting one another. Filter element 26 may have a generally cylindrical shape, and the diameter thereof may be essentially equal to the diameter of the tobacco rod. The ends of the filter element 26 permit the passage of air and smoke therethrough.

A ventilated or air diluted smoking article can be provided with an optional air dilution means, such as a series of perforations 30, each of which extend through the tipping material and plug wrap. The optional perforations 30 can be made by various techniques known to those of ordinary skill in the art, such as laser perforation techniques. Alternatively, so-called off-line air dilution techniques can be used (e.g., through the use of porous paper plug wrap and pre-perforated tipping paper). The formulations of the invention can be incorporated within any of the components of a smoking article, including but not limited to, as a component of the tobacco charge, as a component of the wrapping paper (e.g., included within the paper or coated on the interior or exterior of the paper), as an adhesive, as a filter element component, and/or within a capsule located in any region of the smoking article.

The formulations of the invention can also be incorporated into aerosol-generating devices that contain nicotine and/or tobacco material (or some portion or component thereof) that is not intended to be combusted during use, including so-called "e-cigarettes". Some of these types of smoking articles employ a combustible fuel source that is burned to provide an aerosol and/or to heat an aerosol-forming material. Others employ battery-powered heating elements to heat an aerosol-forming composition. Exemplary references that describe smoking articles of a type that generate flavored vapor, visible aerosol, or a mixture of flavored vapor and visible aerosol, include those set forth in US Pat. Pub. No. 2012/0192880 to Dube et al., which is incorporated by reference herein.

The formulations of the invention can be incorporated into smokeless tobacco products, such as loose moist snuff (e.g., snus); loose dry snuff; chewing tobacco; pelletized tobacco pieces; extruded or formed tobacco strips, pieces, rods, cylinders or sticks; finely divided ground powders; finely divided or milled agglomerates of powdered pieces and components; flake-like pieces; molded tobacco pieces; gums; rolls of tape-like films; readily water-dissolvable or water-dispersible films or strips; meltable compositions; lozenges; pastilles; or capsule-like materials possessing an outer shell and an inner region. Various types of smokeless tobacco products are described or referenced in US Pat. Pub. No 2012/0152265 to Dube et al., which is incorporated herein by reference.

Figure 4:
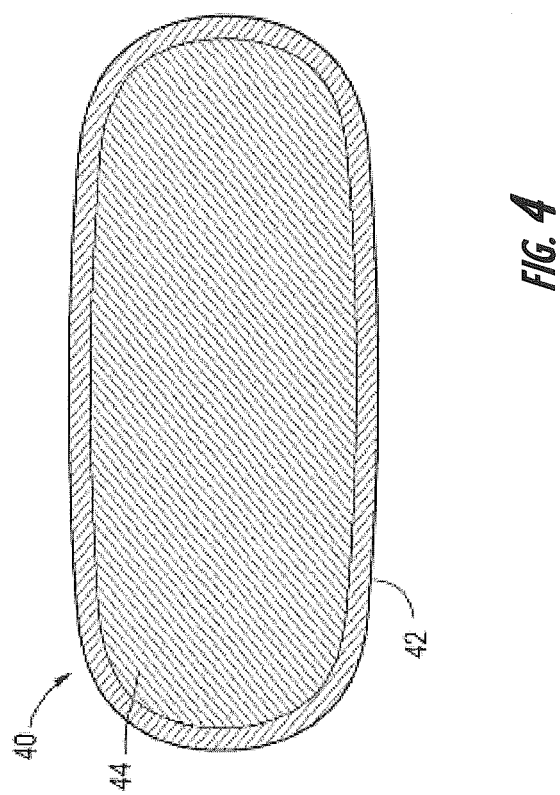
FIG. 4 is a cross-sectional view of a smokeless tobacco product embodiment, taken across the width of the product, showing an outer pouch filled with a smokeless tobacco composition of the invention.

Referring to FIG. 4, a representative snus type of tobacco product comprising a formulation of the present invention is shown. In particular, FIG. 4 illustrates a smokeless tobacco product 40 having a water-permeable outer pouch 42 containing a smokeless tobacco composition 44. Any of the components of the tobacco product can comprise a tobacco-derived material as described herein (e.g., the interior or exterior of the pouch lining or a portion of the smokeless tobacco composition contained therein).

Many exemplary smokeless tobacco compositions that can benefit from use of the formulations of the invention comprise shredded or particulate tobacco material that can serve as a carrier for the sugar-enriched, tobacco-derived materials of the invention. The smokeless tobacco compositions of the invention can also include a water-soluble polymeric binder material and optionally other ingredients that provide a dissolvable composition that will slowly disintegrate in the oral cavity during use. In certain embodiments, the smokeless tobacco composition can include lipid components that provide a meltable composition that melts (as opposed to merely dissolving) in the oral cavity, such as compositions set forth in US Pat. Pub. No. 2012/0037175 to Cantrell et al., which is incorporated by reference herein.

In one particular smokeless tobacco product embodiment, a composition of the invention is added to a non-tobacco plant material, such as a plant material selected from potato, beet (e.g., sugar beet), grain, pea, apple, and the like. The non-tobacco plant material can be used in a processed form. In certain preferred embodiments, the non-tobacco plant material can be used in an extracted form, and as such, at least a portion of certain solvent soluble components are removed from that material. The non-tobacco extracted plant material is typically highly extracted, meaning a substantial amount of the aqueous soluble portion of the plant material has been removed. See, for example, US Pat. Pub. No. 2011/0247640 to Beeson et al, which is incorporated by reference herein.

Further ingredients can be admixed with, or otherwise incorporated within, the smokeless tobacco compositions according to the invention. The ingredients can be artificial, or can be obtained or derived from herbal or biological sources. Exemplary types of ingredients include salts (e.g., sodium chloride, potassium chloride, sodium citrate, potassium citrate, sodium acetate, potassium acetate, and the like), natural sweeteners (e.g., fructose, sucrose, glucose, maltose, vanillin, ethylvanillin glucoside, mannose, galactose, lactose, and the like), artificial sweeteners (e.g., sucralose, saccharin, aspartame, acesulfame K, neotame and the like), organic and inorganic fillers (e.g., grains, processed grains, puffed grains, maltodextrin, dextrose, calcium carbonate, calcium phosphate, corn starch, lactose, manitol, xylitol, sorbitol, finely divided cellulose, and the like), binders (e.g., povidone, sodium carboxymethylcellulose and other modified cellulosic types of binders, sodium alginate, xanthan gum, starch-based binders, gum arabic, lecithin, and the like), pH adjusters or buffering agents (e.g., metal hydroxides, preferably alkali metal hydroxides such as sodium hydroxide and potassium hydroxide, and other alkali metal buffers such as metal carbonates, preferably potassium carbonate or sodium carbonate, or metal bicarbonates such as sodium bicarbonate, and the like), colorants (e.g., dyes and pigments, including caramel coloring and titanium dioxide, and the like), humectants (e.g., glycerin, propylene glycol, and the like), effervescing materials such as certain acid/base combinations, oral care additives (e.g., thyme oil, eucalyptus oil, and zinc), preservatives (e.g., potassium sorbate, and the like), syrups (e.g., honey, high fructose corn syrup, and the like), disintegration aids (e.g., microcrystalline cellulose, croscarmellose sodium, crospovidone, sodium starch glycolate, pregelatinized corn starch, and the like), flavorant and flavoring mixtures, antioxidants, and mixtures thereof. Exemplary encapsulated additives are described, for example, in WO 2010/132444 to Atchley, which has been previously incorporated by reference herein.

See also, the smokeless tobacco ingredients set forth in US Pat. Pub. Nos. 2012/0055494 to Hunt et al. and 2012/0199145 to Byrd et al., which are incorporated by reference herein.

The amount of the sugar-enriched, tobacco-derived materials of the present invention incorporated within a tobacco composition or tobacco product can depend on the desired function of the sugar-enriched, tobacco-derived material, the chemical makeup of the sugar-enriched, tobacco-derived material, and the type of tobacco composition to which the sugar-enriched, tobacco-derived material is added. The amount of sugar-enriched, tobacco-derived material added to a tobacco composition can vary, but will typically not exceed about 50 weight percent based on the total dry weight of the tobacco composition to which the composition is added. For example, the amount of sugar-enriched, tobacco-derived material added to a tobacco composition may be in the range of about 0.25 to about 25 weight percent or about 1 to about 10 weight percent, based on the total dry weight of the tobacco composition.

Although the use of such sugar-enriched, tobacco-derived materials is generally described in the context of tobacco compositions, it is noted that such formulations can be applicable in many other types of compositions. For example, sugar-enriched tobacco materials of the invention can be used in foods or beverages or otherwise incorporated into a dietary supplement intended for oral consumption. Additional uses include cosmetic and pharmaceutical compositions.

EXPERIMENTAL

Aspects of the present invention is more fully illustrated by the following examples, which are set forth to illustrate certain aspects of the present invention and are not to be construed as limiting thereof.

Example 1

A slurry is formed by adding water to cured tobacco leaf and the cured leaf slurry is steeped overnight (about 20 hours). The slurry is homogenized by a disintegrator and passed into a horizontal screw press for liquid extraction, giving a brown liquid sugar-containing extract. The extract is clarified by processing on a 0.1 µm ceramic filter using tangential flow filtration and washed with water. The permeate is cooled and subjected to 1 kDa ultrafiltration using tangential flow filtration and then concentrated using reverse osmosis filtration (using a reverse osmosis membrane). NaOH is added to adjust the pH of the extract to about 8.4 or greater. A kettle vacuum evaporator is used to concentrate the sample in batches, giving three batches of sugar-enriched extract. In the first two batches, it was noted that nicotine was not removed from the extract with the water. The pH of the third batch is re-adjusted to ensure that it is above 8.4, which allowed the nicotine to be removed from the extract with the water (giving a sample with 0.5% nicotine by weight). The three batches thus obtained had total solids values of 54%, 67%, and 61%, respectively. A composite sample of the combined extract had a total solids value of 67.7% and a nicotine concentration of 1.57% by weight.

Example 2

A slurry is formed by adding hot water to cured tobacco leaf and the cured leaf slurry is steeped overnight (about 20 hours), giving a darker water color than in Example 1. The slurry is homogenized by a disintegrator and passed into a horizontal screw press for liquid extraction, giving a brown liquid sugar-containing extract. The extract is clarified by processing on a 0.1 μm ceramic filter using tangential flow filtration and washed with water. The permeate is subjected to 1 kDa ultrafiltration using tangential flow filtration and then to reverse osmosis filtration to concentrate. NaOH is added to adjust the pH of the extract to about 8.4 or greater. A kettle vacuum evaporator is used to concentrate the sample in batches. A composite sample of the combined extract had a total solids value of 85.77% and a nicotine concentration of 0.79% by weight.

Example 3

A slurry is formed by adding water to cured tobacco leaf and the cured leaf slurry is steeped overnight (about 20 hours). The slurry is homogenized by a disintegrator and passed into a horizontal screw press for liquid extraction, giving a brown liquid sugar-containing extract. The extract is clarified by processing on a 0.1 μm ceramic filter using tangential flow filtration and washed with water. The permeate is subjected to 1 kDa ultrafiltration using tangential flow filtration and then to reverse osmosis filtration to concentrate. NaOH is added to adjust the pH of the extract to about 8.4 or greater. A kettle vacuum evaporator is used to concentrate the sample in batches. pH adjustments were conducted as necessary to maintain the pH of the batches at or above 8.4 prior to beginning vacuum evaporation. A composite sample of the combined extract had a total solids value of 84.23% and a nicotine concentration of 1.24% by weight.

Example 4

Tobacco plants are harvested and homogenized by adding water to the plants in a disintegrator. The homogenized mixture is then passed into a horizontal screw press for liquid extraction, giving a liquid, sugar-containing extract. The extract is cooled and the pH is adjusted to about 7.5 by the addition of NaOH. The sugar-containing extract is clarified by processing on a 0.1 μm ceramic filter using tangential flow filtration. The permeate is subjected to 1 kDa ultrafiltration and then to reverse osmosis filtration to concentrate. NaOH is added to adjust the pH of the extract to above 8.4. A kettle vacuum evaporator is used to concentrate the sample, giving a sugar-enriched extract. The extract had a total solids value of 84% and a nicotine content of 0.5%.

Example 5

Tobacco plants are harvested and homogenized by adding a buffer (75 mM glycine at pH 10) to the plants in a disintegrator. The homogenized mixture is then passed into a horizontal screw press for liquid extraction, giving a liquid, sugar-containing extract. The extract is cooled and the pH is adjusted to about 7.5 by the addition of NaOH. The sugar-containing extract is clarified first by passing the extract through a decanter. A filtering agent (diatomaceous earth) is added to the supernatant, the mixture is stirred for 15 minutes, and then passed through a filter press. The filtrate is further clarified by processing on a 0.1 μm ceramic filter using tangential flow filtration. The permeate is subjected to 1 kDa ultrafiltration and then to reverse osmosis filtration to concentrate. NaOH is added to adjust the pH of the extract to above 8.4. A kettle vacuum evaporator is used to concentrate the sample, giving a sugar-enriched extract. The extract had a total solids content of 72.84% and a nicotine content of 0.67%.

Example 6

Tobacco plants are harvested and homogenized by adding water to the plants in a disintegrator. The homogenized mixture is then passed into a horizontal screw press for liquid extraction, giving a liquid, sugar-containing extract. The extract is fed to a kettle in batches, where each batch is boiled and cooked for about 30 minutes, producing solids that are removed by a strainer. The combined extract is further clarified by processing on a 0.1 μm ceramic filter using tangential flow filtration. The permeate is subjected to 1 kDa ultrafiltration and then to reverse osmosis filtration to concentrate. NaOH is added to adjust the pH of the extract to above 8.4. A kettle vacuum evaporator is used to concentrate the sample, giving a sugar-enriched extract. The extract had a total solids value of 61.30%.

Example 7

Tobacco plants are harvested, chipped, and homogenized by adding a buffer (75 mM glycine at pH 10) to the plants in a disintegrator. The homogenized mixture is then passed into a horizontal screw press for liquid extraction, giving a liquid, sugar-containing extract. The pH of the extract is adjusted to about 7.1 by the addition of NaOH. A filtering agent (diatomaceous earth) is added to the supernatant, the mixture is stirred for 15 minutes, and then passed through a filter press. The filtrate is further clarified by 500 kDa a ultrafiltration followed by 1 kDa ultrafiltration, and then is subjected to reverse osmosis filtration to concentrate. NaOH is added to adjust the pH of the extract to above 8.4. A kettle vacuum evaporator is used to concentrate the extract, giving a sugar-enriched extract with a representative total solids level of 88%.

Example 8

Tobacco plants are harvested, leaves are stripped from the stalks, and the leaves are homogenized by adding buffer (75 mM glycine at pH 10.5) to the leaves in a disintegrator. The homogenized mixture is then passed into a horizontal screw press for liquid extraction, giving a liquid, sugar-containing extract. The extract is clarified by processing on a 0.1 μm ceramic filter using tangential flow filtration. A filtering agent (diatomaceous earth) is added to the filtrate, the mixture is stirred for 15 minutes, and then passed through a filter press. The resulting liquid is further clarified using 1 kDa ultrafiltration, and then subjected to reverse osmosis filtration to concentrate. NaOH is added to adjust the pH of the extract to above 8.4. A kettle vacuum evaporator is used to concentrate the extract, giving a sugar-enriched extract with a representative total solids content of 88%.

Example 9

Tobacco plants are harvested by pulling the stalk and root out of the ground and low pressure water is used to clean the roots. The tobacco material is put through a chopper and the material is homogenized by adding water to the chopped material in a disintegrator. The homogenized mixture is then passed into a horizontal screw press for liquid extraction, giving a liquid, sugar-containing extract. The extract is clarified by processing on a 0.1 μm ceramic filter using tangential flow filtration. The filtrate is further clarified using 1 kDa ultrafiltration, and is then concentrated by reverse osmosis filtration. NaOH is added to adjust the pH of the extract to above 8.4. A kettle vacuum evaporator is used to concentrate the extract, giving a sugar-enriched extract with a representative total solids content of 60.74%.

Example 10

Tobacco plants are harvested, leaves are stripped from the stalks, and the leaves are homogenized by adding buffer (75 mM glycine at pH 10.5) to the leaves in a disintegrator. The homogenized mixture is then passed into a horizontal screw press for liquid extraction, giving a liquid, sugar-containing extract. A filtering agent (diatomaceous earth) is added to the extract, the mixture is stirred for 15 minutes, and then passed through a filter press. The filtrate is further clarified by 500 kDa ultrafiltration followed by 1 kDa ultrafiltration, and then subjected to reverse osmosis filtration to concentrate. NaOH is added to adjust the pH of the extract to above 8.4. A kettle vacuum evaporator is used to concentrate the extract, giving a sugar-enriched extract with a representative total solids content of 82.07%.

Example 11

Tobacco stalks are harvested, chopped, and homogenized by adding water to the plants in a disintegrator. The homogenized mixture is then passed into a horizontal screw press for liquid extraction, giving a liquid, sugar-containing extract. The extract is clarified by processing on a 0.1 μm ceramic filter using tangential flow filtration. The filtrate is further clarified by 1 kDa ultrafiltration, and concentrated by reverse osmosis filtration. NaOH is added to adjust the pH of the extract to above 8.4. A kettle vacuum evaporator is used to concentrate the extract, giving a sugar-enriched extract with a representative total solids content of 92.11%.

Example 12

Tobacco plants are harvested, leaves are stripped from the stalks, and the leaves are homogenized by adding water to the leaves in a disintegrator. The homogenized mixture is then passed into a horizontal screw press for liquid extraction, giving a liquid, sugar-containing extract. The extract is processed on a 0.1 μm ceramic filter using tangential flow filtration, giving a filtrate and a retentate. The retentate is added to a kettle vacuum with water and the resulting mixture is pH adjusted to about 1.8 with HCl. The retentate mixture is boiled to break down the starch contained therein for about 6 hours. Enzymes can be added (e.g., amyloglucosidase and/or alpha amylase) to break the starch more completely down into glucose. The kettle-cooked mixture is processed on a 0.1 μm ceramic filter using tangential flow filtration. The permeate therefrom is then processed by 1 kDa ultrafiltration and concentrated by reverse osmosis filtration. The kettle cooked material (i.e., comprising starch converted to glucose) is combined with the extracted sugar material and the combined solution is again processed by 1 kDa ultrafiltration and concentrated using reverse osmosis filtration. NaOH is added to adjust the pH of the permeate to above 8.4. A kettle vacuum evaporator is used to concentrate the sample, giving a sugar-enriched extract having a total solids content of 90.1%.

Example 13

Tobacco plants are harvested, leaves are stripped from the stalks, and the leaves are homogenized by adding water to the leaves in a disintegrator. The homogenized mixture is then passed into a horizontal screw press for liquid extraction, giving a liquid, sugar-containing extract. The extract is processed on a 0.1 μm ceramic filter using tangential flow filtration, giving a filtrate and a retentate. Water is added to make a 30% solids solution from the retentate. The pH of the mixture is adjusted to 1.80 using HCl and the pH-adjusted mixture is boiled for 4 hours (adding pH 1.80 water as necessary to keep a constant liquid volume). The pH is further adjusted to 5.5 and α-amylase is added in an amount of 0.1% by volume. The mixture is gently agitated for 2 hours, after which time the pH is adjusted to 5.0, the mixture is heated to 37° C., and amyloglucosidase is added in an amount of 0.5% by volume to the mixture.

The resulting mixture is run through a 0.1 μm ceramic filter to retain and remove enzymes and the permeate is processed by 1 kDa ultrafiltration. The permeate is concentrated by reverse osmosis filtration and vacuum filtration to give a sugar-enriched extract.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims Although specific terms are employed herein, they are used in a generic and descriptive sense only and not for purposes of limitation.

What is claimed:

1. A method for preparing a sugar-enriched extract from a plant of the *Nicotiana* species or portion thereof, comprising:
   receiving a plant material of the *Nicotiana* species;
   contacting the plant material with a solvent for a time and under conditions sufficient to extract one or more sugars from the plant material into the solvent and form a liquid sugar-containing extract;
   separating a solid extracted plant material from the liquid sugar-containing extract;
   clarifying the liquid sugar-containing extract to form a clarified sugar-containing extract and a solids fraction;
   adjusting the pH of the clarified sugar-containing extract to a pH of at least 8; and
   isolating the clarified sugar-containing extract to give a sugar-enriched extract comprising at least 10% fructose and glucose by dry weight.

2. The method of claim 1, wherein the plant material of the *Nicotiana* species comprises green plant material, yellowed plant material, cured plant material, or a combination thereof.

3. The method of claim 1, further comprising concentrating the clarified sugar-containing extract to provide a concentrated sugar-enriched extract.

4. The method of claim 3, wherein the concentrated sugar-enriched extract is in the form of a liquid, semi-solid, or solid.

5. The method of claim 3, wherein the concentrating step provides a concentrated sugar-enriched extract having a total solids content of at least 50%.

6. The method of claim 3, wherein the concentrating is done using one or more of reverse osmosis, vacuum evaporation, and atmospheric heating.

7. The method of claim 1, further comprising adding one or more components to remove color, odor, taste, alkaloids, metals, or a combination thereof, at any step of the process.

8. The method of claim 7, wherein the one or more components are selected from the group consisting of activated carbon, a resin, clay, a chelating agent, a molecularly imprinted polymer, a non-imprinted polymer, or a combination thereof.

9. The method of claim 1, wherein the sugar-enriched extract comprises at least 20% fructose and glucose by dry weight.

10. The method of claim 1, wherein the solvent comprises water.

11. The method of claim 1, wherein the clarifying step comprises filtering the liquid sugar-containing extract.

12. The method of claim 10, wherein the filtering comprises one or more of microfiltration, ultrafiltration, and nanofiltration.

13. The method of claim 1, wherein the at least 10% fructose and glucose comprises at least 50% fructose by weight in the absence of any further treatment to convert any portion of glucose to fructose.

14. The method of claim 1, further comprising:
treating the solids fraction obtained from the clarifying step to convert at least a portion of the starch contained therein to sugar to give a treated solids fraction; and
concentrating the treated solids fraction.

15. The method of claim 14, further comprising combining the treated solids fraction with the sugar-enriched extract.

16. The method of claim 14, wherein the treating step comprises one or both of heating the solids fraction at an acidic pH and adding one or more enzymes to the solids fraction.

17. The method of claim 16, wherein the one or more enzymes are selected from the group consisting of α-amylase, amyloglucosidase, and xylose isomerase.

18. The method of claim 16, wherein the heating comprises boiling.

19. The method of claim 14, further comprising filtering the treated solids fraction prior to said concentrating.

20. The method of claim 14, wherein the concentrating step provides a product in the form of a liquid, semi-solid, or solid.

21. A method for preparing a sugar-enriched extract from a plant of the *Nicotiana* species or portion thereof, comprising:
receiving a plant material of the *Nicotiana* species;
pressing the plant material in the absence of added liquid and collecting a liquid sugar-containing extract released from the pressed plant material;
separating a solid plant material from the liquid sugar-containing extract;
clarifying the liquid sugar-containing extract to form a clarified sugar-containing extract and a solids fraction;
adjusting the pH of the clarified sugar-containing extract to a pH of at least 8; and
isolating the clarified sugar-containing extract to give a sugar-enriched extract comprising at least 10% fructose and glucose by dry weight.

22. The method of claim 1, wherein the at least 10% fructose and glucose comprises at least 30% fructose by weight in the absence of any further treatment to convert any portion of glucose to fructose.

23. The method of claim 1, wherein the at least 10% fructose and glucose comprises at least 40% fructose by weight in the absence of any further treatment to convert any portion of glucose to fructose.

24. The method of claim 1, wherein the solvent comprise a buffer.

* * * * *